United States Patent [19]
Braun et al.

[11] Patent Number: 4,837,330
[45] Date of Patent: Jun. 6, 1989

[54] PREPARATION OF SULFATOBETAINES

[75] Inventors: Gerold Braun, Ludwigshafen; Chung-Ji Tschang, Bad Duerkheim; Christos Vamvakaris, Kallstadt; Klaus Glaser, Mutterstadt, all of Fed. Rep. of Germany

[73] Assignee: BASF Aktiengesellschaft, Ludwigshafen, Fed. Rep. of Germany

[21] Appl. No.: 168,241

[22] Filed: Mar. 15, 1988

[30] Foreign Application Priority Data

Mar. 20, 1987 [DE] Fed. Rep. of Germany ....... 3709216

[51] Int. Cl.$^4$ ................. C07D 211/82; C07D 213/18; C07D 291/00; C07D 233/54
[52] U.S. Cl. ............................. 546/339; 260/501.21; 544/2; 546/347; 548/341
[58] Field of Search ...................... 260/501.21; 544/2; 546/339, 347; 548/341

[56] References Cited

U.S. PATENT DOCUMENTS 3,274,204  9/1966  Klass et al. .................... 546/339

FOREIGN PATENT DOCUMENTS 1906851  2/1969  Fed. Rep. of Germany ...... 546/339

Primary Examiner—Mary C. Lee
Assistant Examiner—Robert C. Whittenbaugh
Attorney, Agent, or Firm—Oblon, Fisher, Spivak, McClelland & Maier

[57] ABSTRACT

Sulfatobetaines are prepared by reacting an adduct of a base having a tertiary N atom and sulfur trioxide with an alkylene oxide in the presence of an alkylene carbonate as a solvent.

9 Claims, No Drawings

PREPARATION OF SULFATOBETAINES

The present invention relates to a process for the preparation of sulfatobetaines by reacting an adduct of a base having a tertiary N atom and sulfur trioxide with an alkylene oxide in the presence of an alkylene carbonate as a solvent.

U.S. Pat. No. 3,274,204 describes the preparation of sulfatobetaines by reacting an epoxide with a complex of a tertiary amine and sulfur trioxide, by reacting a cyclic sulfate with a tertiary amine or by reacting an epoxide with a complex of dioxane and sulfur trioxide and then reacting the product with a tertiary amine.

As is evident from the description and the Examples, these processes are advantageously carried out in the presence of an inert solvent, such as toluene, hexane or ethylene dichloride, which may not be completely toxicologically acceptable. Furthermore, it has been found that the processes described are not always satisfactory with regard to the yield and purity of the products obtained. Particularly in the reaction of a complex of a tertiary amine and sulfur trioxide with ethylene oxide in ethylene dichloride as the solvent preferably used in the Examples of the stated U.S. Patent, side reactions may take place, leading to impurities and to discoloration. When hekane is used as the inert solvent, the amine/$SO_3$ complexes are frequently not sufficiently soluble, so that the reaction to give the desired sulfatobetaine is very sluggish. These disadvantages also apply to the process described in German LaidOpen Application DOS No. 1,906,851.

German Published Application DAS No. 1,191,652 discloses that, for example, pyridinium ethylsulfate (2-pyridinium-1-sulfatoethane) can be prepared in an expensive manner by reacting hydroxyethylpyridinium chloride, obtained from pyridine and ethylene chlorohydrin, with chlorosulfonic acid. In this procedure too, the yield and purity are unsatisfactory.

German Patent Application No. 36 35 230.6 proposes reacting the complex of a tertiary amine and sulfur trioxide not with an alkylene oxide but with an alkylene carbonate as the alkylating agent. This procedure requires relatively high temperatures of from 80° to 220° C.

In order to be able to carry out the reaction in the lower range of the stated temperatures, the reaction must be catalyzed by a base. The lower the temperature, the larger the amount of base required as a catalyst. The advantage of these reactions is that no free alkylene oxide occurs. However, in order to avoid side reactions and discoloration of the end product, vanishing of the $SO_3$ adduct used, ie. its conversion, must be monitored precisely in the course of the reaction.

It is an object of the present invention to provide a very simple and convenient process for the largescale industrial production of sulfatobetaines.

We have found that this object is achieved by a process for the preparation of sulfatobetaines of the formula I

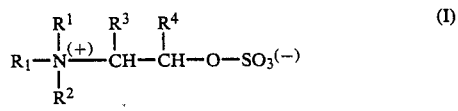

where the individual radicals $R^1$ and $R^2$ may be identical or different and are each a saturated straight-chain or branched alkyl radical of 1 to 22 carbon atoms, a cycloalkyl radical where the ring is of 5 to 7 carbon atoms, phenyl, naphthyl or aralkyl having a total of 7 to 12 carbon atoms, and moreover the two radicals $R^1$, together with the N atom, may form a 5-membered or 6-membered heterocyclic ring which may contain one or more further hetero atoms and may contain a fused benzene ring, and $R^2$ is alkyl of 1 to 4 carbon atoms, or the two radicals $R^1$, together with the N atom and the radical $R^2$, form a 5-membered or 6-membered unsaturated heterocyclic ring which may contain one or more further hetero atoms and may contain a fused benzene ring, $R^3$ and $R^4$ are identical or different and $R^3$ is hydrogen, alkyl of 1 to 7 carbon atoms, $-CH_2Cl$ or $-CH_2-OR^5$, where $R^5$ is a straight-chain or branched alkyl radical of 1 to 18 carbon atoms or phenyl, and $R^4$ is hydrogen, alkyl of 1 to 20 carbon atoms or phenyl, and $R^3$ and $R^4$ are interchangeable, from an adduct of a base having a tertiary N atom and sulfur trioxide, wherein an amine/$SO_3$ adduct of the formula II

where $R^1$ and $R^2$ have the meanings stated for formula I, is reacted with an alkylene oxide of the formula III

where $R^3$ and $R^4$ have the meanings stated for formula I, at from 40° to 150° C., preferably from 60° to 90° C., in the presence of ethylene carbonate or 1,2-propylene carbonate, or a mixture of these, as an inert solvent.

The process according to the invention gives sulfatobetaines in a surprisingly simple manner and in excellent yield, and pure end products which crystallize out as crystal white compounds during the reaction. Chlorohydrocarbons and other solvents in which the starting complex frequently cannot be dissolved completely, so that a suspension is employed, can be avoided. The procedure is carried out in true solution and, in comparison with the process of Patent Application No. P 36 35 230.6, no base catalysis and precise reaction monitoring is necessary and the reaction can also be carried out at low temperatures.

It was not to be expected that, under the conditions used, the ethylene carbonate or 1,2-propylene carbonate would be a stable solvent which does not participate in the reaction. The amine/$SO_3$ complex of the formula II can be prepared, advantageously and without complications, directly in these solvents to be used according to the invention.

Specifically, the following may be stated regarding the novel process:

Examples of tertiary amines as starting compounds for the amine/$SO_3$ adducts of the formula II are tridodecyl-, tristearyl-, tricyclohexyl-, triphenyl-, dimethyldodecyl-, diethylphenyl-, dimethylstearyl-, trimethyl-, triethyl- and tributylamine.

The preferred tertiary alkylamines include tertiary amines having alkyl radicals of 1 to 4 carbon atoms in the case of $R^1$ and 12 to 18 carbon atoms in the case of $R^2$.

Preferred adducts are those of sulfur trioxide with heterocyclic compounds. Examples of noteworthy heterocyclic compounds are N-methyl- and N-ethylpiperidine, N-methyl- and N-ethylmorpholine, N-methylpyrazole, oxazole, isoxazole, acridine, phenacridine, pyrazine and pyridazine.

Particularly preferred compounds are pyridine which is unsubstituted or substituted by one or two alkyl radicals of 1 to 4 carbon atoms, by a carboxyalkyl group where alkyl is of 1 to 4 carbon atoms or by a nitrile group, e.g. α-, β- or γ-picoline, 2-ethylpyridine, methyl nicotinate or nicotinonitrile, quinoline or isoquinoline, which may be substituted by methyl, such as quinaldine, and N-($C_1$—$C_{12}$-alkyl)-imidazoles which are unsubstituted or substituted at one of the carbon atoms by alkyl of 1 to 6 carbon atoms or phenyl, eg. N-methyl- and Nethylimidazole, 1,2-dimethylimidazole, N-methyl-2-phenylimidazole or 1-dodecylimidazole.

The $SO_3$ adducts of the formula II can be prepared in a conventional manner or, particularly advantageously, in the solvent to be used according to the invention.

The ethylene carbonate or 1,2-propylene carbonate, or a mixture of these, is advantageously used in the novel reaction in an amount of from 20 to 50, preferably from 30 to 40%, by weight, based on the weight of the amine/$SO_3$ complex. This means that, at the temperatures employed, the reaction can be carried out in very concentrated solutions, which is advantageous for an industrial reaction.

The epoxides of the formula III are in principle known. They are advantageously used in a molar ratio of from 1:1 to 1:1.5, preferably from 1:1.2 to 1:1.3, based on the amine/$SO_3$ adduct of the formula II, ie. an excess of from 20 to 30 mol % of epoxide leads to optimum yields.

Examples of epoxides of the formula III are ethylene oxide, propylene oxide, 1,2- and 2,3-butylene oxide, styrene oxide, n-butyl glycidyl ether, 2-ethylhexyl glycidyl ether and epichlorohydrin.

As stated above, the reaction of a compound of the formula II with an alkylene oxide of the formula III is carried out at from 40° to 150° C., preferably from 60° to 90° C.

The reaction is as a rule complete in the course of from 0.5 to 4 hours, depending on the temperature.

The betaines, which are generally obtained in crystalline form, can be isolated in a simple manner by filtration under suction. After washing with a solvent, such as ethanol or methanol, virtually analytically pure products are obtained.

The compounds prepared by the novel process can be used as surfactants, in particular in detergents, as assistants in the textile sector or as electroplating assistants, wetting agents, emulsifiers or dispersants.

In particular, heterocyclic sulfatoethanes which are excellent brightening agents when used as electroplating assistants are readily obtainable by the novel process. Examples of these are pyridiniumsulfatoethane, quinoliniumsulfatoethane, 1-pyridinium-2-methyl-2-sulfatoethane, 1-pyridinium-2-ethyl-2-sulfatoethane and 1-pyridinium-2-methyleneoxy-n-butyl-2-sulfatoethane.

EXAMPLE 1

1-pyridinium-2-sulfatoethane 237 parts of pyridine and 792 parts of ethylene carbonate are initially taken at 40° C. in a stirred kettle. Thereafter, 240 parts of $SO_3$ are metered in at no higher than 70° C. for the preparation of the adduct. 160° parts of ethylene oxide are then added at 75° C., while cooling. When the pyridine/$SO_3$ adduct has been completely converted, the mixture is cooled to 40° C. Excess ethylene oxide is removed, after which the crystalline reaction product is separated from the solvent, washed with methanol and then dried.

Melting point: 203° C.
Yield: 90%.

EXAMPLE 2

1-(N-methylimidazoiium)-2-sulfatoethane 41 parts of N-methylimidazole and 200 parts of propylene carbonate are initially taken in a stirred kettle. Thereafter, 40 parts of $SO_3$ are metered in at about 50° C. for the preparation of the adduct. 55 parts of ethylene oxide are then added at 90° C., while cooling. When the reaction is complete, the mixture is cooled to room temperature. The product is isolated by filtering it off from the solvent under suction, washing it with methanol and drying it.

Melting point: 205° C.
Yield: 91%.

EXAMPLE 3

1-pyridinium-2-phenyl-2-sulfatoethane 250 parts of propylene carbonate and 39 parts of pyridine are initially taken in a stirred kettle. The pyridine/$SO_3$ adduct is obtained by metering in 40 parts of $SO_3$. 72 parts of styrene oxide are metered in as described in Example 2. After the mixture has been cooled, the reaction product is isolated as described in Example 2.

Melting point: 213° C.
Yield: 85%.

EXAMPLE 4

1-pyridinium-2-methyleneoxy-n-butyl-2-sulfatoethane

The compound is prepared as described in Example 3. However, 90 parts of n-butyl glycidyl ether are used instead of styrene oxide.

Yield: 80%.
Melting point: 217° C.

We claim:

1. A process for the preparation of a sulfatobetaine of the formula:

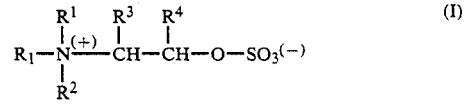

wherein radicals $R^1$ and $R^2$ are identical or different and each is a saturated straight-chain or branched alkyl radical 1–22 carbon atoms, a cycloalkyl radical of 5–7 carbon atoms, phenyl, naphthyl or $C_{7-12}$ aralykyl, or the two $R^1$ radicals, together with the nitrogen atom, form a 5-membered or 6-membered heterocyclic ring which may contain at least one additional heteroatom and may contain a fused benzene ring, and $R^2$ is $C_{1-4}$ alkyl, or the two $R^1$ radicals together with the N atom and the radical $R^2$ form a 5-membered or 6-membered unsaturated heterocyclic ring which may contain at least one additional heteroatom and may contain a fused benzene ring, $R^3$ and $R^4$ are identical or different and $R^3$ is hydrogen, $C_{1-7}$ alkyl, —$CH_2Cl$ or —CH- $_2$—OR$^5$, wherein R$^5$ is a straight-chain or branched C$_{1-18}$ alkyl or phenyl, and R$^4$ is hydrogen, C$_{1-20}$ alkyl or phenyl, and R$^3$ and R$^4$ are interchangeable, which comprises:

reacting an adduct of a base having a tertiary N atom and sulfur trioxide having the formula (II):

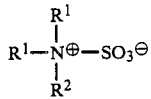
(II)

wherein R$^1$ and R$^2$ are as defined above, with an alkylene oxide of the formula (III):

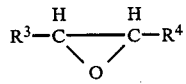
(III)

wherein R$^3$ and R$^4$ each have the meaning stated above at from 40°–150° C. in the presence of ethylene carbonate or 1,2-propylene carbonate, or a mixture thereof as an inert solvent.

2. The process of claim 1, wherein said adduct is a heterocyclic adduct of sulfur trioxide with pyridine which is unsubstituted or substituted by at least one C$_{1-4}$ alkyl radical, a carboxy (C$_{1-4}$) alkyl radical or a nitrile group, or with quinoline or isoquinoline, either of which is unsubstituted or substituted by methyl, or with a N-(C$_1$–C$_{12}$ alkyl)imidazole, which is unsubstituted or substituted on one of the carbon atoms by a C$_{1-6}$ alkyl group or phenyl.

3. The process of claim 1, wherein the amount of ethylene carbonate or 1,2-propylene carbonate, or a combination thereof employed ranges from 20–50% by weight, based on the amine/SO$_3$ adduct.

4. The process of claim 3, wherein the amount of said solvent ranges from 30–40% by weight.

5. The process of claim 2, wherein the molar ratio of epoxide to amine/SO$_3$ adduct ranges from 1:1 to 1:1.5.

6. The process of claim 5, wherein said ratio ranges from 1:1.2 to 1:1.3.

7. The process of claim 1, wherein said epoxide is ethylene oxide, propylene oxide, 1,2- or 2,3-butylene oxide, styrene oxide, N-butyl glycidyl ether, 2-ethylhexyl glycidyl ether or epichlorohydrin.

8. The process of claim 1, wherein the temperature of reaction ranges from 60°–90° C.

9. The process of claim 1, wherein said adduct is a pyridine/sulfur trioxide adduct which is reacted with ethylene oxide.

* * * * *